(12) United States Patent
Wantink et al.

(10) Patent No.: US 8,840,743 B2
(45) Date of Patent: Sep. 23, 2014

(54) SOFT TIP BALLOON CATHETER

(75) Inventors: Kenneth L. Wantink, Temecula, CA (US); Jeong S. Lee, Diamond Bar, CA (US); Justin K. Mann, Murrieta, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 13/609,968

(22) Filed: Sep. 11, 2012

(65) Prior Publication Data
US 2014/0074020 A1    Mar. 13, 2014

(51) Int. Cl.
*B32B 37/12* (2006.01)
*A61M 31/00* (2006.01)

(52) U.S. Cl.
USPC ........ 156/86; 156/198; 156/204; 604/103.06; 604/103.08

(58) Field of Classification Search
USPC ...................... 604/96.01, 103, 103.06, 103.07
See application file for complete search history.

(56) References Cited

U.S. PATENT DOCUMENTS

| | | | | |
|---|---|---|---|---|
| 4,944,745 A | * | 7/1990 | Sogard et al. | 606/194 |
| RE34,633 E | * | 6/1994 | Sos et al. | 600/585 |
| 5,458,615 A | | 10/1995 | Klemm et al. | |
| 5,478,320 A | * | 12/1995 | Trotta | 604/103.06 |
| 5,507,768 A | | 4/1996 | Lau et al. | |
| 5,733,301 A | * | 3/1998 | Forman | 606/192 |
| 5,827,225 A | * | 10/1998 | Ma Schwab | 604/96.01 |
| 6,187,130 B1 | * | 2/2001 | Berard et al. | 156/294 |
| 6,217,547 B1 | | 4/2001 | Lee | |
| 6,277,093 B1 | | 8/2001 | Lee | |
| 6,620,127 B2 | | 9/2003 | Lee et al. | |
| 6,692,461 B2 | * | 2/2004 | Wantink | 604/103 |
| 7,001,420 B2 | | 2/2006 | Speck et al. | |
| 7,074,206 B2 | | 7/2006 | Lee et al. | |
| 7,087,039 B1 | * | 8/2006 | Cox et al. | 604/96.01 |
| 7,815,599 B2 | * | 10/2010 | Griffin et al. | 604/96.01 |
| 7,828,766 B2 | | 11/2010 | Durcan | |
| 7,906,066 B2 | | 3/2011 | Wilson et al. | |
| 7,951,259 B2 | * | 5/2011 | Duchamp et al. | 156/294 |

(Continued)

FOREIGN PATENT DOCUMENTS

| | | | |
|---|---|---|---|
| EP | 0 184 314 | | 6/1986 |
| EP | 1 192 970 | | 4/2002 |
| JP | 02271873 A | * | 11/1990 |
| JP | 05253304 A | * | 10/1993 |

OTHER PUBLICATIONS

International Search Report and Written Opinion for PCT/US2013/054564, dated Oct. 29, 2013.

*Primary Examiner* — William Bell
(74) *Attorney, Agent, or Firm* — Baker Botts LLP

(57) ABSTRACT

Method for fabricating a balloon catheter including providing an inner tubular member having a distal section and a distal end with a lumen extending therein and forming a balloon having a distal leg with a first segment having a first diameter and a first wall thickness and a second segment having a second wall thickness. The second diameter is greater than the first diameter and the first wall thickness is greater than the second wall thickness. The distal end section of the inner tubular member can be positioned in the balloon and bonded to the first segment while reducing the diameter of the second segment. Method also provided for fabricating a multilayer balloon catheter including removing at least a portion of an outer layer from the distal leg of the balloon.

24 Claims, 9 Drawing Sheets

(56) References Cited

U.S. PATENT DOCUMENTS

| | | |
|---|---|---|
| 7,967,836 B2 | 6/2011 | Warnack et al. |
| 8,052,638 B2 | 11/2011 | Lee et al. |
| 2002/0072707 A1* | 6/2002 | Gonzalez et al. ........ 604/103.06 |
| 2005/0131445 A1* | 6/2005 | Holman et al. ............... 606/194 |
| 2007/0142771 A1* | 6/2007 | Durcan .................... 604/103.06 |
| 2008/0004658 A1* | 1/2008 | Malecki et al. ............... 606/213 |
| 2008/0262470 A1 | 10/2008 | Lee et al. |
| 2009/0156998 A1 | 6/2009 | Arana et al. |
| 2012/0065718 A1 | 3/2012 | Simpson et al. |
| 2012/0296273 A1 | 11/2012 | Arana et al. |
| 2012/0302994 A1 | 11/2012 | Wilson et al. |

\* cited by examiner

SOFT TIP BALLOON CATHETER

BACKGROUND

1. Field

The presently disclosed subject matter relates to intraluminal balloon catheters for use in percutaneous transluminal coronary angioplasty (PTCA) or stent delivery systems or the like. Particularly, the disclosed subject matter relates to a balloon catheter and system having an improved distal tip.

2. Description of Related Art

Intraluminal balloon catheters are well known and beneficial for a variety of medical uses, including diagnostics, therapeutics, and treatment. For example, and not limitation, balloon catheters can be used for a number of different vascular and/or coronary applications. In percutaneous transluminal coronary angioplasty (PTCA) procedures, a guidewire is typically advanced into the coronary artery until the distal end of the guidewire crosses a lesion to be dilated. A dilatation catheter having an inflatable balloon on the distal portion thereof is advanced into the coronary anatomy over the guidewire until the balloon of the dilatation catheter is properly positioned across the lesion. Once properly positioned, the dilatation balloon is inflated with inflation fluid one or more times to a predetermined size to open up the vascular passageway. Generally, the inflated diameter of the balloon is approximately the same diameter as the native diameter of the body lumen being dilated so as to complete the dilatation, but not over-expand the artery wall. After the balloon is finally deflated, blood flow resumes through the dilated artery and the dilatation catheter and the guidewire can be removed therefrom.

In addition to or as an alternative of angioplasty procedures, it may be desirable to implant an intravascular prosthesis, generally called a stent, inside the artery at the site of the lesion. Stents may also be used to repair vessels having an intimal flap or dissection or to generally strengthen a weakened section of a vessel or to maintain its patency. Stents are usually delivered to a desired location within a coronary artery in a contracted condition on a balloon of a catheter, which is similar or identical in many respects to a balloon angioplasty catheter. The balloon, and thus the stent, is expanded within the patient's artery to a larger diameter. The balloon is deflated to remove the catheter with the stent implanted at the site of the dilated lesion. See for example, U.S. Pat. No. 5,507,768 (Lau et al.) and U.S. Pat. No. 5,458,615 (Klemm et al.), each of which is hereby incorporated by reference in its entirety.

It is desirable to provide an intraluminal catheter with a soft distal tip to prevent or minimize injury to the vessel during advancement of the catheter therein. One challenge has been forming a connection between the soft tip and the catheter. For example, the joint or connector needs to be sufficiently strong to prevent disengagement of the soft tip, and yet prevent kinking at the junction between the soft tip and catheter shaft. Additionally, it is beneficial to balance the strength of the connection between the soft tip and the catheter shaft with the need to minimize the stiffness of the distal end of the catheter. Minimizing the stiffness of the distal end of the catheter results in improved maneuverability of the catheter.

Accordingly, there remains a need to provide a catheter with a soft tip having improved performance.

SUMMARY

In accordance with one aspect of the disclosed subject matter, a method of fabricating a balloon catheter includes providing an inner tubular member having a distal section, a distal end, and a lumen extending therein. A balloon is formed with a working length, a distal neck, and a distal leg, the distal leg having a first segment with a first diameter and first wall thickness and a second segment with a second diameter and second wall thickness. As described herein, the second diameter is larger than the first diameter and the second wall thickness is thinner than the first wall thickness. The distal end of the inner tubular member is positioned in the balloon, with the first segment of the distal leg disposed proximate the distal section of the inner tubular member and the second segment of the distal leg extending distally beyond the distal end of the inner tubular member. Heat is applied to the distal leg of the balloon to bond at least a portion of the first segment to the distal section of the inner tubular member and to reduce the second diameter of the second segment of the distal leg.

In one embodiment, forming the balloon can include melt-extruding a thermoplastic polymeric material to form a tube having a distal leg, the distal leg having a first segment and a second segment, and cooling the extruded tube to a temperature less than an elevated temperature of the melt-extrusion. The extruded tube can be placed within a capture member or mold, having a first portion with a first diameter and a second portion with a second diameter, and blown or expanded to the desired configuration. The polymeric material of the extruded tube further can be biaxially oriented by radially expanding the extruded tube with pressurized media in the tube lumen and axially expanding the extruded tube with a load applied on at least one end of the tube.

In one embodiment, the method can include positioning a mandrel in the lumen of the inner tubular member such that the mandrel extends beyond the second segment of the distal leg of the balloon. A heat shrink tubing can be positioned around the outside of at least the first and second segments of the distal leg of the balloon. Heat can be applied to the heat shrink tubing and distal leg of the balloon so as to shrink the heat shrink tubing to force the second segment of the distal leg onto the mandrel. The mandrel can have a tapered or contoured shape to form a corresponding shape of the distal leg.

In accordance with another aspect of the disclosed subject matter, a method of fabricating a multilayer balloon catheter includes providing an inner tubular member having a distal section, a distal end, and a lumen extending therein. A multilayer balloon is formed having at least a first layer and a second layer, a working length, a distal neck, and a distal leg, the distal leg having a first segment and a second segment. The first layer is made of a first polymer material having a first durometer and the second layer is made of a second polymer material having a second durometer. The second layer is an outer layer relative to the first layer and the second durometer is harder than the first durometer. At least a portion of the second layer is removed from at least the distal leg of the balloon. The distal section of the inner tubular member is positioned in the balloon, with at least the second segment of the distal leg extending beyond the distal leg of the inner tubular member. The first distal leg segment of the balloon is bonded to the inner tubular member.

In one embodiment, the first layer can comprise Pebax having a first durometer between about 55 D and about 63 D and the second layer can comprise Pebax having a second durometer between about 70 D Pebax and about 72 D Pebax. The portion of the second layer can be removed with a rotary device. For example, a rotary device and support mandrel can rotate the balloon shaft and a cutting bit can remove a portion of the second layer.

In one embodiment, the multilayer balloon can be formed such that the second segment of the distal leg has a diameter greater than the first segment of the distal leg. A portion of the second layer can be removed from the second segment. A mandrel can be positioned in the inner lumen of the inner tubular member so as to extend beyond the second segment of the distal leg of the balloon. A heat shrink tubing can be positioned around the outside of the first and second segments. Heat can be applied to the heat shrink tubing and the distal leg to bond at least a portion of the first segment to the distal section of the inner tubular member. The heat shrink tubing can force the second segment onto the mandrel, thus reducing the diameter of the distal leg to form a monolithic distal dip.

It is to be understood that both the foregoing general description and the following detailed description are exemplary and are intended to provide further explanation of the disclosed subject matter.

The accompanying drawings, which are incorporated in and constitute part of this specification, are included to illustrate and provide further understanding of the disclosed subject matter. It will be appreciated that the drawings are not to scale, and are provided for purposes of illustration only. Together with the description, the drawings serve to explain the principles of the disclosed subject matter.

DETAILED DESCRIPTION

Figure 1:
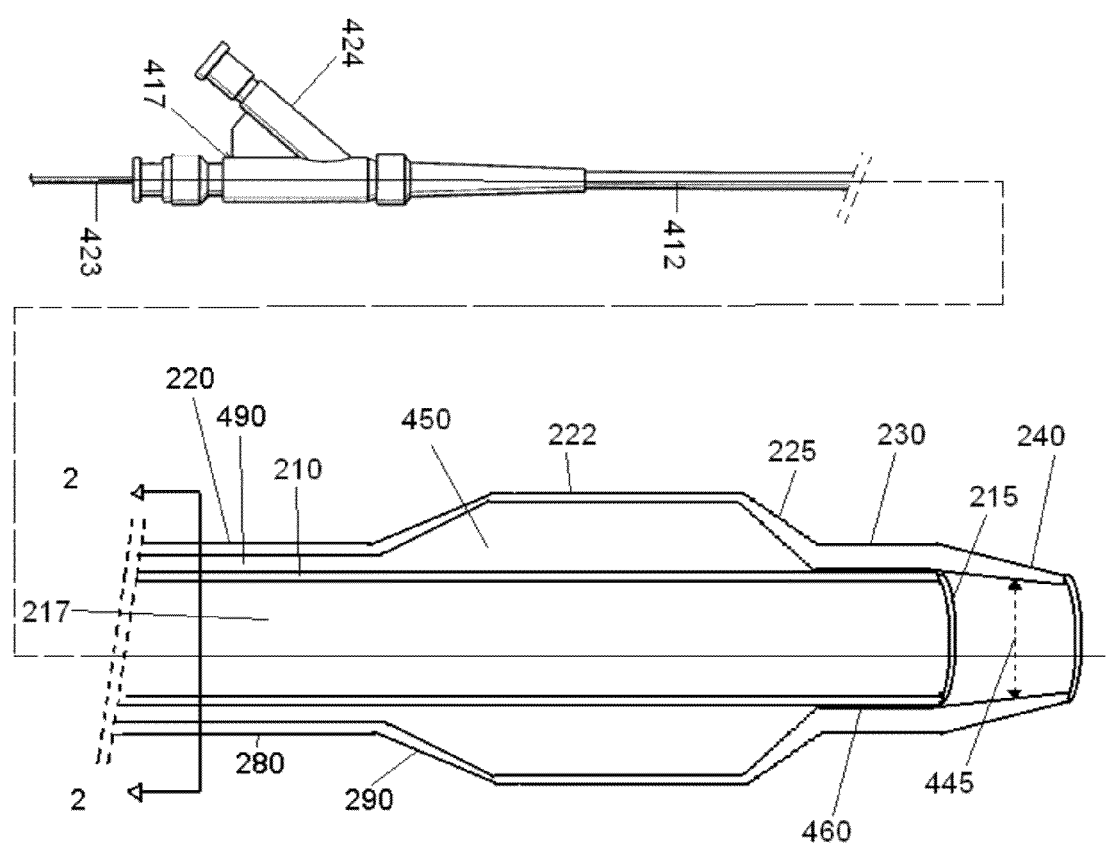
FIG. 1 schematically depicts a representative embodiment of a balloon catheter in accordance with certain aspects of the disclosed subject matter with the distal portion of the balloon catheter enlarged and in cross-section.

While the presently disclosed subject matter will be described with reference to a few specific embodiments, the description is illustrative of the disclosed subject matter and is not to be construed as limiting. Various modifications to the presently disclosed subject matter can be made to the preferred embodiments by those skilled in the art without departing from the true spirit and scope of the disclosed subject matter as defined by the appended claims. It will be noted here that for a better understanding, like components are designated by like reference numerals throughout the various figures.

In accordance with one aspect of the disclosed subject matter, a method of fabricating a balloon catheter includes providing an inner tubular member having a distal section, a distal end, and a lumen extending therein. A balloon is formed with a working length, a distal neck, and a distal leg, the distal leg having a first segment with a first diameter and first wall thickness and a second segment with a second diameter and second wall thickness. As disclosed herein, the second diameter is larger than the first diameter and the second wall thickness is thinner than the first wall thickness. The distal end of the inner tubular member is positioned in the balloon, with the first segment of the distal leg disposed proximate the distal section of the inner tubular member and the second segment of the distal leg extending distally beyond the distal end of the inner tubular member. Heat is applied to the distal leg of the balloon to bond at least a portion of the first segment to the distal section of the inner tubular member and to reduce the second diameter of the second segment of the distal leg.

Particular embodiments of this aspect of the disclosed subject matter are described below, with reference to the figures, for purposes of illustration, and not limitation. For purposes of clarity, the balloon catheter and the method of fabricating the balloon catheter are described concurrently and in conjunction with each other.

A balloon catheter produced according to the disclosed subject matter will now be described, for purposes of illustration and not limitation, with reference to FIGS. 1 and 2. The balloon catheter generally comprises an elongated catheter shaft at least including an inner tubular member 210 extending a length thereof; see (110) in FIG. 3 and FIG. 5. The inner tubular member 210 has a distal section 212, a distal end 215, and a lumen 217 extending therein. The inner tubular member 210 can be composed of, for example, multi-layered tubing having lubricious inner liner and bondable outer layer such as nylon or Pebax® polyether block amide (hereinafter Pebax), or any of other suitable materials for the intended purpose. Other examples of suitable materials are identified in U.S. Pat. Nos. 6,277,093 and 6,217,547, each of which is hereby incorporated by reference in its entirety. The elongated catheter shaft has a proximal shaft section 412 with an inflation lumen 490 and, if desired, a guidewire lumen 217 defined therein. An adapter 417 having an arm 424 can be disposed on a proximal end of the catheter shaft for providing access to the inflation lumen 490. The arm 424 thereby can be configured to be connected to a source of inflation fluid (not shown). Additionally, for over-the-wire embodiments as described further, the adapter 417 can be configured for access to the guidewire lumen 217. The guidewire 423 can be introduced through the adapter 417 into the guidewire lumen 217.

Figures 2A, 2B:
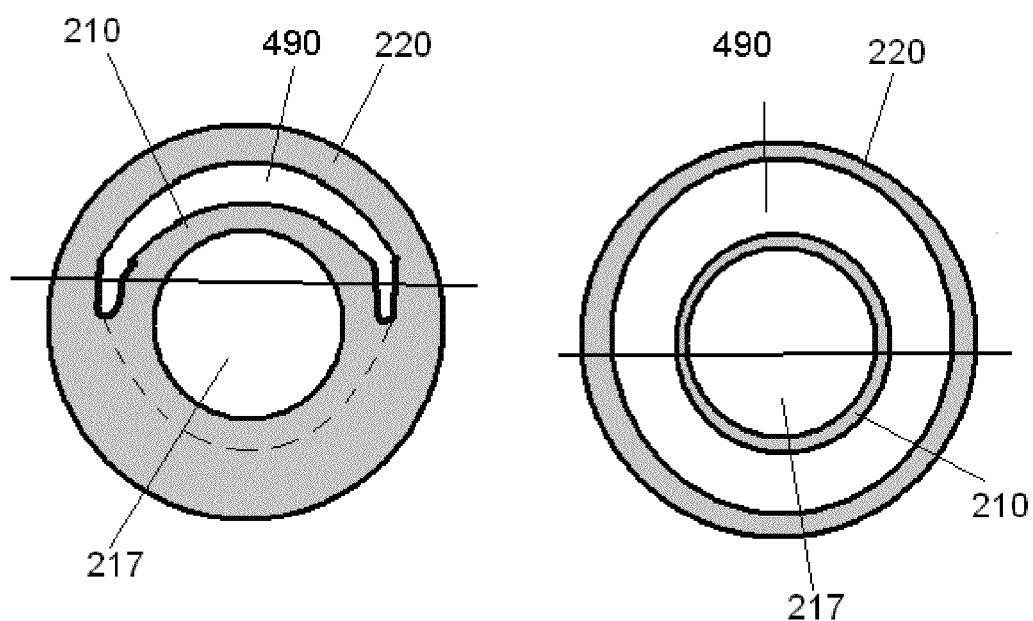
FIG. 2A and FIG. 2B are transverse cross-sectional views of alternative embodiments of the catheter shaft along line 2-2.

In one embodiment, conventionally known as an over-the-wire catheter, the elongated inner tubular member 210 can have a guidewire lumen 217 extending therein such that the guidewire 423 can extend from the adapter 417 through the lumen 217 and distally beyond a distal end of the catheter. Alternatively, the guidewire lumen can extend along only a distal portion of the inner tubular member. Such a configuration is conventionally known as a rapid exchange balloon catheter, which generally includes a short guidewire lumen extending to the distal end of the shaft from a guidewire port located distal to the proximal end of the shaft. Additional configurations and adaptations are disclosed in U.S. Pat. No. 8,052,638, which is hereby incorporated by reference in its entirety. As depicted in FIG. 1, for purpose of illustration and not limitation, a balloon 220 is disposed at a distal end 215 of the inner tubular member 210. The balloon includes an inner chamber 450 defined within a working length of the balloon, a distal neck 225 and a proximal neck 290. The interior chamber 450 of the balloon 220 is in fluid communication with the inflation lumen 490 extending the length of the catheter shaft member 412. For example, and with reference to FIG. 2A and FIG. 2B, the inflation lumen can be defined within the inner tubular member 210, such as a dual lumen configuration as is known in the art and depicted in FIG. 2A. Alternatively, the inflation lumen can be defined as an annular space 490 between the inner tubular member 210 and an outer tubular member as depicted in FIG. 2B and generally known as a coaxial arrangement. As embodied herein, at least the working length 222 of the balloon is disposed concentrically around the inner tubular member 210. In this manner, and regardless of whether a dual lumen or a coaxial arrangement is provided, when a pressurizing medium is introduced into through the inflation lumen 490 the balloon can expand.

For purpose of illustration and not limitation, and with reference to a coronary balloon catheter, the length of the balloon catheter disclosed herein can generally be about 108 to about 200 centimeters, preferably about 135 to about 150 centimeters, and typically about 140 centimeters for PTCA, and can have other suitable dimensions for other various applications. The inner tubular member can have, for purpose of example and not limitation, an OD of about 0.43 mm to about 0.66 mm, and an ID of about 0.38 mm to about 0.46 mm depending on the diameter of the guidewire to be used with the catheter. For purpose of example and not limitation, the balloon can have a length of about 8 mm to about 100 mm, and an inflated working diameter of about 1.5 mm to about 15 mm.

Figure 3:
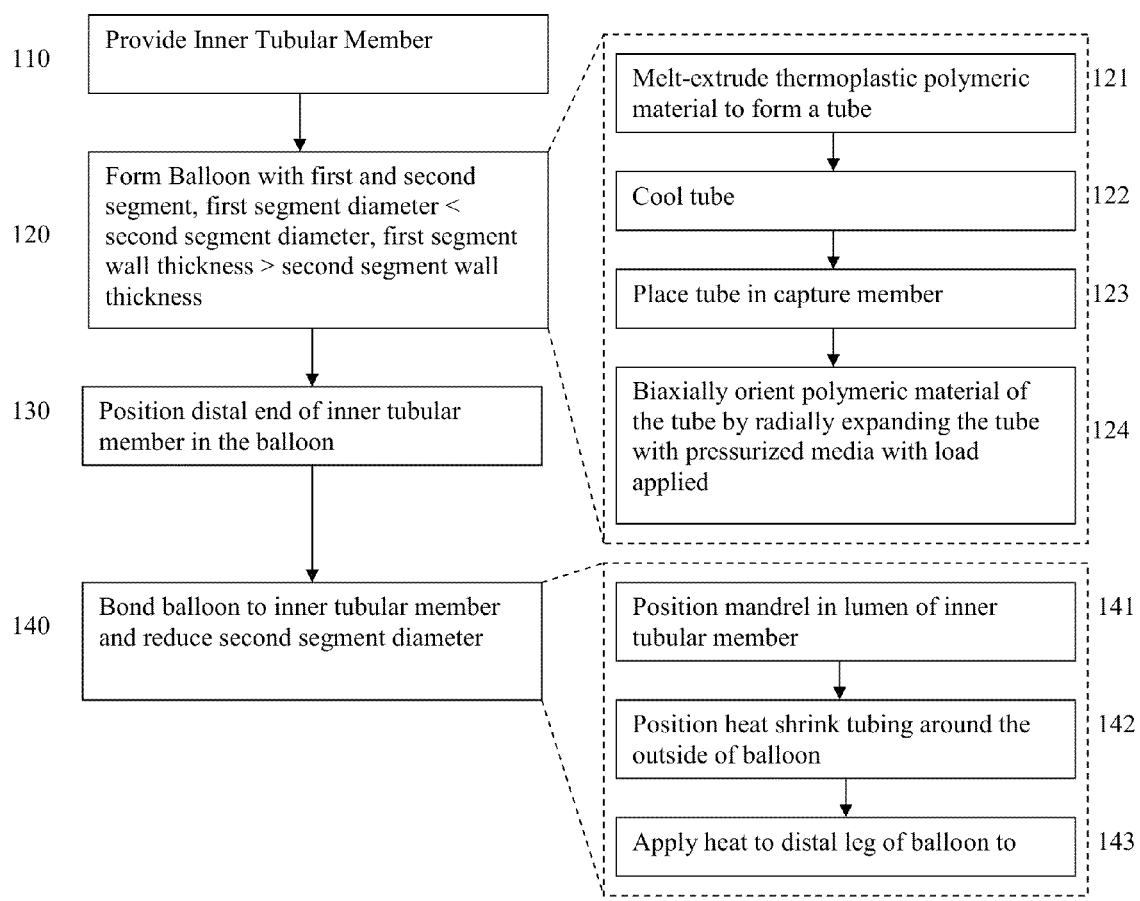
FIG. 3 is a flow diagram of a method of fabricating a balloon catheter according to one embodiment of the disclosed subject matter.
Figure 5:
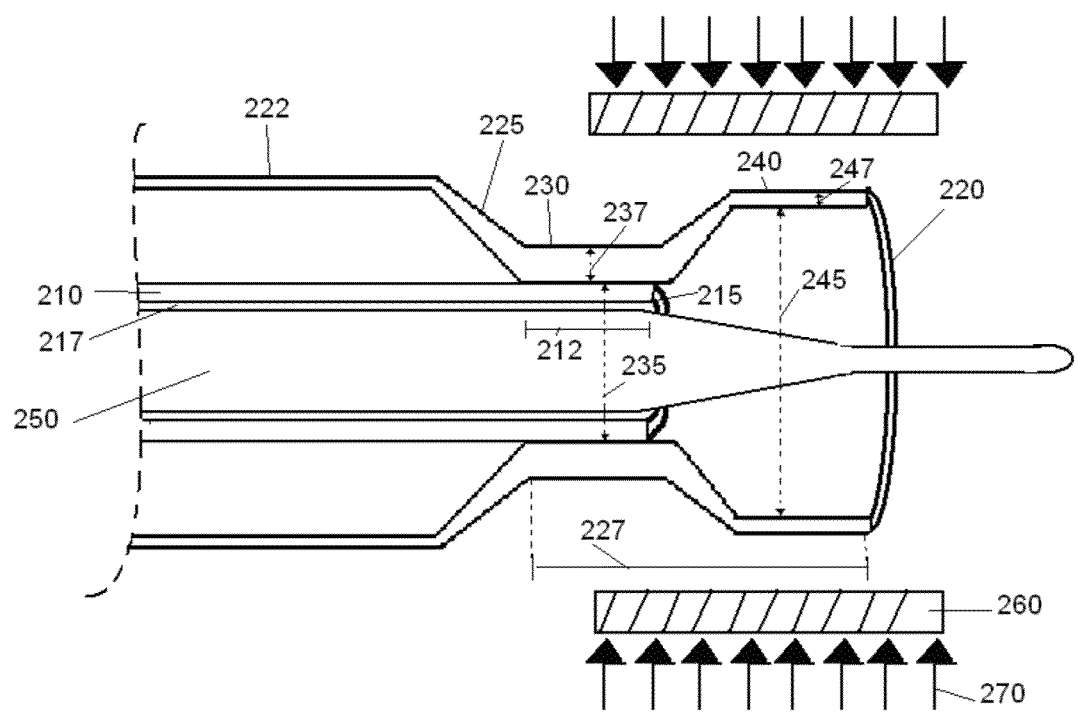
FIG. 5 is a longitudinal cross-sectional view of a schematic representation of portion of a balloon catheter being fabricated in accordance with the disclosed subject matter.

In accordance with one aspect of the disclosed method, a balloon is formed as noted at (120) in FIG. 3. As shown in FIG. 5, a balloon 220 is formed (120) with a working length 222, a distal neck 225, and a distal leg 227. The distal leg 227 has a first segment 230 with a first diameter 235 and a first wall thickness 237. The distal leg has a second segment 240 with a second diameter 245 and a second wall thickness 247. The second diameter 245 is greater than the first diameter 235 and the second wall thickness 247 is thinner than the first wall thickness 237. The balloon can have a proximal neck (not shown in FIG. 5) and a proximal leg (not shown in FIG. 5).

The balloon 220 can be composed of a wide variety of suitable materials, for example, nylon, co-polyamide such as Pebax (poly ether block amide), polyester, co-polyester, polyurethane, polyethylene, or the like. In some embodiments, the balloon 220 can be a multilayer balloon, as discussed in more detail below. More detailed lists of suitable materials are provided in U.S. Pat. Nos. 7,074,206 and 8,052,638., each of which is hereby incorporated by reference in its entirety.

For purpose of example and as embodied herein, the balloon 220 can be formed using a technique similar to that disclosed in U.S. Pat. Nos. 6,620,127, 7,906,066 and 8,052,638, each of which is hereby incorporated by reference in its entirety. In one embodiment, and with reference to FIG. 3 and FIG. 4, the balloon 220 can be formed by melt-extruding (121) a thermoplastic polymeric material to form a tube 320, then blow molding or forming in a mold 350 to a blown balloon having a distal leg 327, the distal leg 327 having a first segment 330 and a second segment 340 at a temperature less than (122) an elevated temperature of the melt-extrusion under high pressure, for example between about 150 and about 500 psi. The extruded tube 320 can be placed (123) within a mold or capture member 350. The extruded tube is radially expanded under suitable conditions by introducing a pressurized fluid into the tube lumen until the outer surface of the extruded tube engages and conforms to the inner surface of the capture member. Furthermore, the polymeric material of the extruded tube 320 can be biaxially oriented (124) by axially expanding the extruded tube 320 with a load applied on at least one end of the tube 320 while radially stretching the extruded tube 320 with a pressurized media in the tube lumen.

In accordance with another aspect, the balloon can be formed using a two stage blow mold process such as disclosed in U.S. Patent Publication No. 2012/0065718, which is hereby incorporated by reference in its entirety. When using the two stage blow mold process, for purposes of example and not limitation, the balloon can be blown initially in a first stage as disclosed in U.S. Patent Publication No. 2002/0065718, with the first and second segments of the distal leg having substantially equal or uniform diameter. In the second stage, however, and as disclosed herein, the second segment of the distal leg can be formed with a diameter larger than the first segment of the distal leg.

Figure 4:
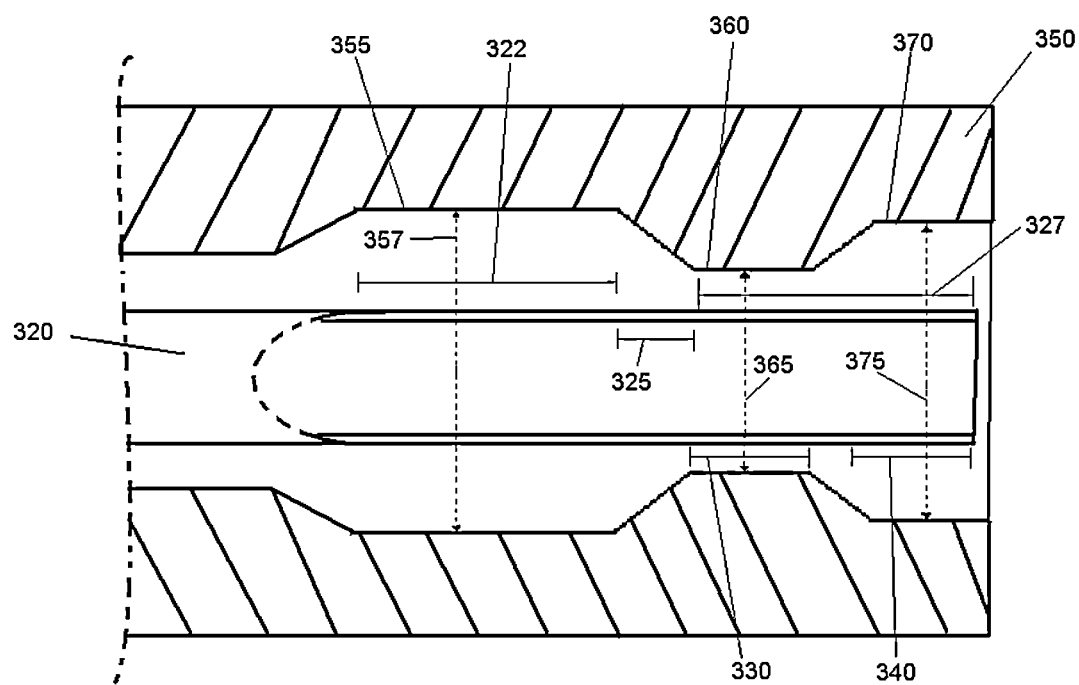
FIG. 4 is a longitudinal cross-sectional view of a melt-extruded tube placed in a capture member to form a balloon according to one embodiment of the disclosed subject matter.

The capture member 350 can have a first portion 360 with a first diameter 365 and a second section 370 with a second diameter 375. The first diameter 365 can be smaller than the second diameter 375 as shown in FIG. 4. When the pressurized media radially expands the tube 320, the first segment 330 of the tube 320 radially expands and conforms to the inner surface of the first portion 360 of the capture member 350. Likewise, the second segment 340 of the tube 320 radially expands and conforms to the inner surface of the second portion 370 of the capture member 350. Because the diameter of the first portion 360 is smaller than the diameter of the second portion 370, the first segment of the resulting balloon will have a diameter less than the second of the resulting balloon. The first segment 330 and second segment 340 of the tube 320 can initially have the same wall thickness. However, as the second segment 340 expands to a greater diameter than the first segment 330, the resulting second segment will have a thinner resulting wall thickness than the resulting wall thickness of the first segment, thereby forming the balloon 220 of FIG. 5.

In like manner, and as illustrated in FIG. 4, the capture member 350 can have a portion 355 having a shape and diameter 357 corresponding to the remainder of the balloon, including the working length 322, the distal neck 325, the proximal neck, and the proximal leg. In this manner, the balloon with the desired leg can be formed in a single capture member 350. Alternatively, one or more separate capture members can be provided, each corresponding to different portions of the balloon. Additionally, the balloon can be formed in a single inflation step, or in additional inflation steps to further stretch and align the polymeric material.

Further in accordance with the disclosed subject matter, and again with reference to FIG. 3 and FIG. 5, the distal end 215 of the inner tubular member 210 is positioned (130) in the balloon 220. The first segment 230 of the distal leg 227 is disposed proximate the distal section 212 of the inner tubular member 210. The second segment 240 of the distal leg 227 extends distally beyond the distal end 215 of the inner tubular member 210. For example, in some embodiments, the distal end 215 of the inner tubular member 210 can be disposed beyond the first segment 230 but not beyond the second segment 240. In other embodiments, the distal section 212 can be disposed such that the distal end 215 is proximate a portion of the first segment 230. As embodied herein, for purposes of illustration and not limitation, the inner tubular member 210 is disposed within the length of the first segment 230 as shown in FIG. 5.

As further embodied herein, and as depicted in the method of FIG. 5, a mandrel 250 can be positioned (141) in the lumen 217 of the inner tubular member 210. The mandrel 250 can, for example, have a tapered or contoured shape such that the portion of the mandrel extending distally beyond the distal end 215 of the inner tubular member 210 decreases in diameter. The mandrel 250 can be positioned to extend beyond the second segment 240 of the distal leg 227 of the balloon 220. The mandrel 250 can be composed of a suitable material, such as metal (e.g., stainless steel or NiTi, coated or uncoated), ceramic, or the like. As embodied herein, the mandrel 250 is composed of Teflon coated or Paralene coated stainless steel which can allow ease of removal after assembly. During the heating process, the shrink tubing forces the softened or molten material of the second segment against the outer surface of the mandrel to conform to the corresponding shape.

Electromagnetic energy, such as thermal, laser, or sonic energy, 270 is applied to the distal leg 227 of the balloon 220 to bond (140) at least a portion of the first segment 230 to the distal section 212 of the inner tubular member 210 and to reduce the second diameter of the second segment 240 of the distal leg 227. Heating (143) the distal leg 227 of the balloon causes the polymeric material of the balloon 220 to soften, or melt and flow. In one embodiment, a heat shrink tubing 260 can be positioned (142) around the outside of at least the first and second segments 230 and 240 of the balloon 220. The heat shrink tubing 260, also referred to as a "heat shrink sleeve", can be composed of a polymeric material configured to shrink when exposed to heat. U.S. Pat. No. 7,951,259, which is hereby incorporated by reference in its entirety, discloses the use of a heat shrink sleeve in fabricating a catheter with a flexible distal end. The heat shrink tubing 260, when heated, shrinks and exerts an inward radial force on the second segment 240. With the polymer of the second segment 240 in a molten or softened, the diameter of the second segment 240 will be reduced by the force exerted by the heat shrink tubing. After the balloon is cooled, the heat shrink tubing is then removed. Heating can be accomplished, for example, by laser heating (e.g., using a CO2 laser), contact heating (e.g., using aluminum nitride, resistance, RF), hot air, resistance heating, induction heating or the like. As embodied herein, for purposes of illustration and not limitation, a solid state laser is used to heat the shrink tubing and soften the first and second segments 230 and 240. As a result, the outer surface of the distal leg 227 can be tapered distally to a smaller outer diameter, while the first segment 230, in its softened or molten state, forms a bond with the distal section 212 of the inner tubular member 210.

Figure 6:
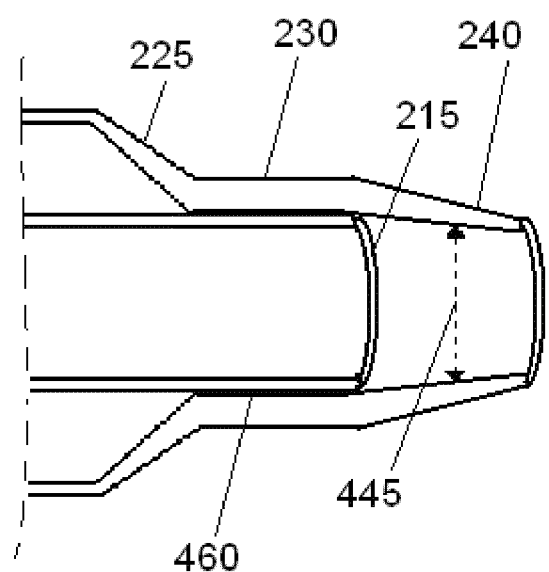
FIG. 6 depicts a longitudinal cross-sectional view of ra representative embodiment of a distal portion of the balloon catheter fabricated according to a method of the presently disclosed subject matter.

FIG. 6 schematically depicts a distal portion of a representative balloon catheter fabricated according to the methods disclosed herein. As previously noted, the inner tubular member 210 can have a guidewire lumen 217 extending distally beyond the tip of the catheter. The balloon has a working length 222, a distal neck 225, and a distal leg comprised of a first segment 230 and a second segment 240. The first segment 230 is bonded to the inner tubular member 210 along a region 460 and generally has a first thickness. The second segment 240, after being heated in accordance with a method of the disclosed subject matter, will have a reduced thickness, at least less than the thickness of the first segment. The resulting thickness of the second segment can be uniform, or as shown in FIG. 6, can be tapered. Furthermore, the second segment can have at least an outer diameter less than the outer diameter of the first segment. Additionally the new diameter of the second segment can taper inwardly, such as depicted in FIG. 6, a diameter 445. The balloon has an interior chamber in fluid communication with the inflation lumen 490, such that when a pressurizing medium is introduced into through the inflation lumen 490 the balloon can expand.

In accordance with another aspect of the disclosed subject matter, a method of fabricating a multilayer balloon catheter includes providing an inner tubular member having a distal section, a distal end, and a lumen extending therein. A multilayer balloon is formed having at least a first layer and a second layer, a working length, a distal neck, and a distal leg, the distal leg having a first segment and a second segment. The first layer is made of a first polymer material having a first durometer and the second layer is made of a second polymer material having a second durometer. The second durometer is greater than the first durometer and the second layer is an outer layer relative to the first layer. At least a portion of the second layer is removed from at least the distal leg of the balloon. The distal section of the inner tubular member is positioned in the balloon, with at least the second segment of the distal leg extending beyond the distal leg of the inner tubular member. The inner tubular member is bonded to the first distal leg segment of the balloon.

Particular embodiments of this aspect of the disclosed subject matter are described below, with reference to the figures, for purposes of illustration, and not limitation. For purposes of understanding, the balloon catheter and the method of fabricating the balloon catheter are described concurrently and in conjunction with each other.

Figure 7:
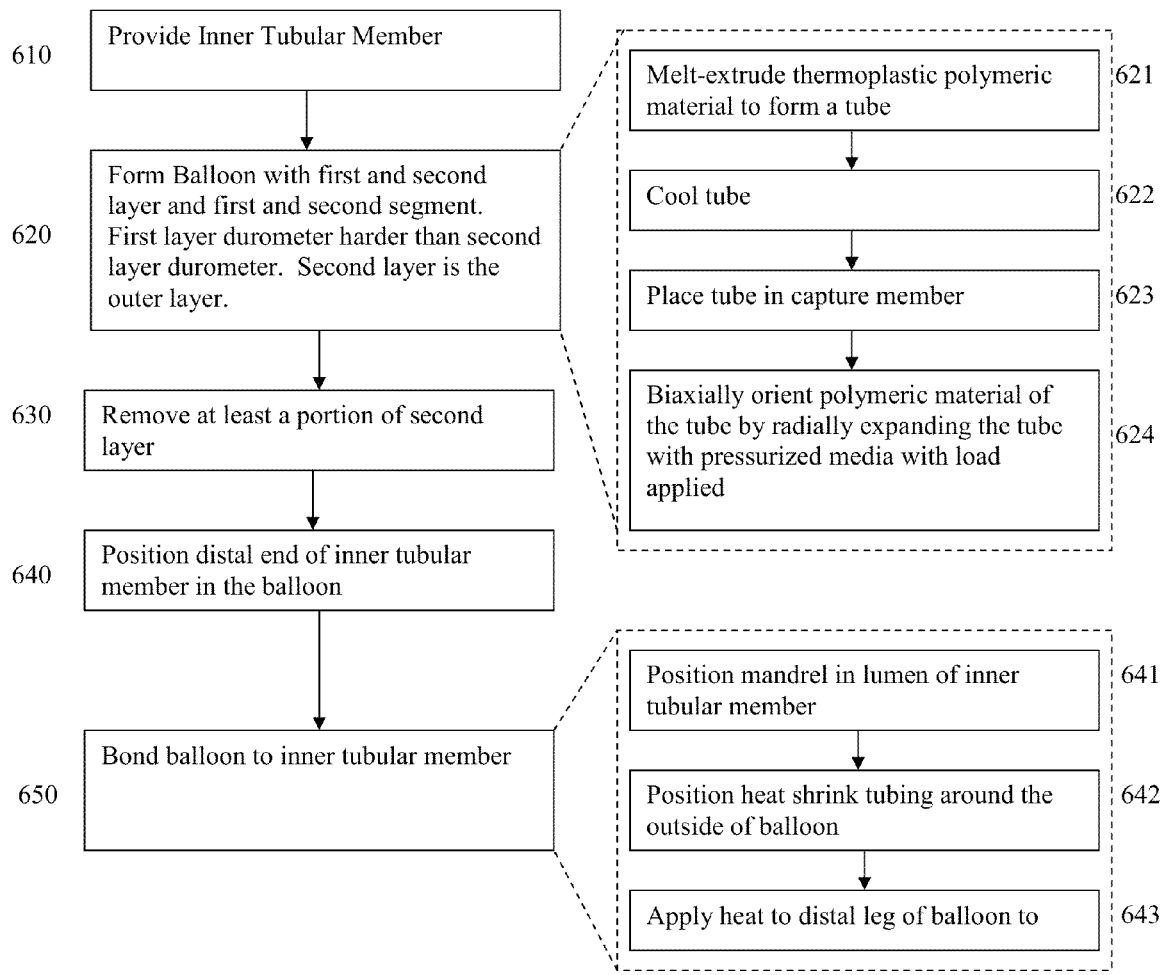
FIG. 7 is a flow diagram of a method of fabricating a multilayer balloon catheter according to another embodiment of the disclosed subject matter.
Figure 9:
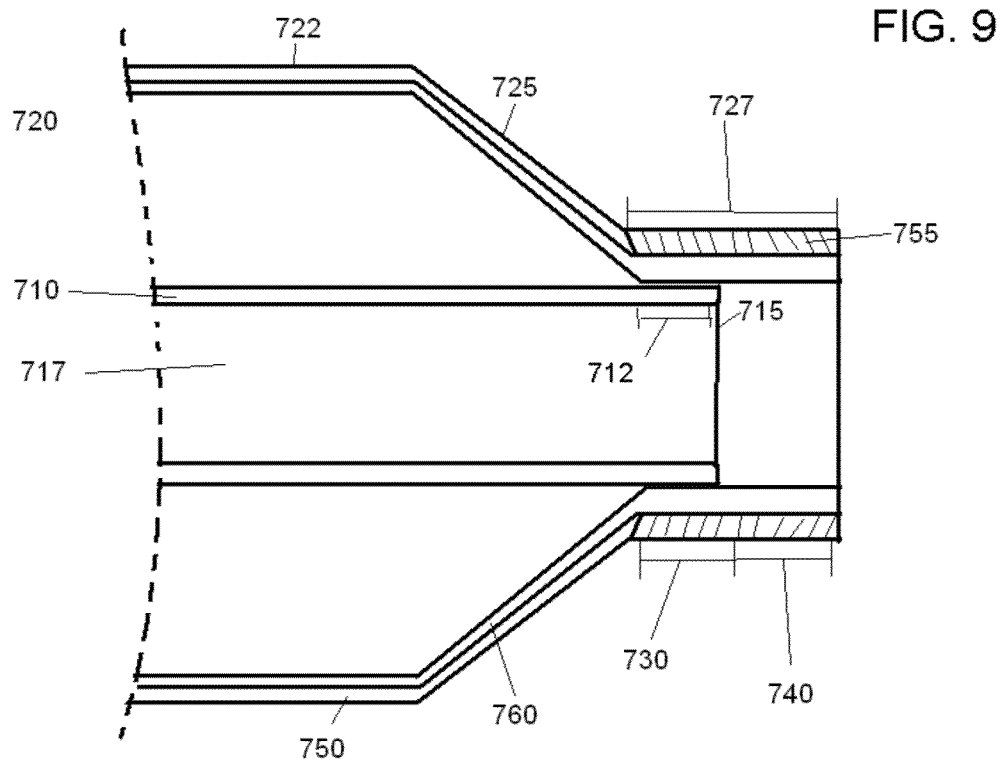
FIG. 9 is a longitudinal cross-sectional view of a schematic representation of a portion of a balloon fabricated according to the method of FIG. 7.

As embodied herein, and with reference to FIG. 7 and FIG. 9, an inner tubular member 710 is provided (610) to form the catheter shaft at least in part. The inner tubular member 710 has a distal section 712, a distal end 715, and a lumen 717 extending therein. As already described herein, the inner tubular member 710 can have same construct as inner tubular member 210. As previously noted, the catheter shaft can be provided with a variety of configurations and constructions, including dual lumen or coaxial configuration and either over-the-wire or rapid exchange guidance configurations.

As further embodied herein, a multilayer balloon 720 is formed (620) with at least a first layer 760 and a second layer 750. The balloon 720 has a working length 722, a distal neck 725, and a distal leg 727 as shown in FIG. 9. The distal leg 727 has a first segment 730 and a second segment 740. The balloon can have a proximal neck 290 and a proximal leg 280 as shown in FIG. 1.

The first layer 760 is made of a first polymer material having a first durometer, and the second layer 750 is made of a second polymer material having a second durometer. As embodied herein, the second durometer is greater than the first durometer, and the second layer is an outer layer relative to the first layer. For example, and not limitation, the balloon embodied herein has a first layer 760 composed of, for example, Pebax having a durometer of between about 55 D and about 63 D. The second layer 750 can be composed of, for example, Pebax having a durometer of between about 70 D and about 72 D Pebax.

Figure 8:
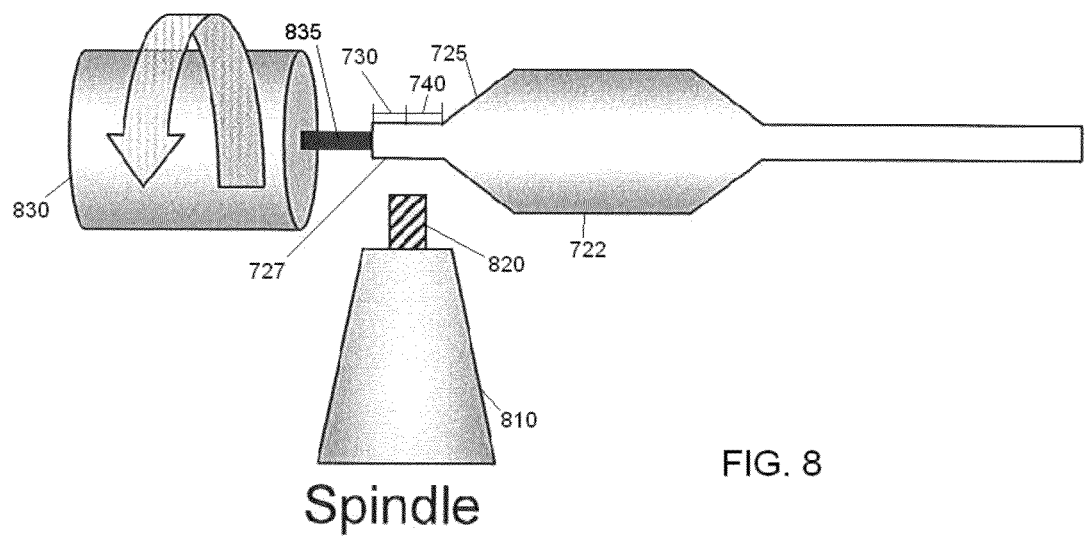
FIG. 8 is a schematic diagram showing removal of at least a portion of a layer of a multilayer balloon according to one embodiment of the disclosed subject matter.

The method disclosed herein includes removing (630) at least a portion 755 of the second layer 750 from the distal leg 727 of the balloon. Various suitable methods for removal of material from the balloon are described in U.S. Pat. No. 7,967,836, which is hereby incorporated by reference in its entirety. In one embodiment of the presently disclosed subject matter, for example, a portion 755 of the second layer 750 can be removed by processing with laser or other thermal ablation process. As embodied herein, with reference to FIG. 8, a rotary device 830 with support mandrel 835 for the balloon shaft can be used to rotate the balloon 720. A high speed spindle 810 with a milling or cutting bit 820 can be used to remove at least a portion 755 of the second layer 750. In some embodiments, for example, a smart camera (not shown) can be used to map the shaft and taper of the balloon 720 to ensure that the balloon is not damaged in the material removal process. The smart camera can, for example, monitor the second layer 750 to determine and control a removal depth. The removal of a portion 755 of the second layer 750 can terminate when the removal depth reaches a predetermined threshold.

In some embodiments, the portion 755 of the second layer 750 that is removed can be limited to the portion of the second layer along the second segment 740 of the distal leg 727 of the balloon. Alternatively, the portion 755 of the second layer 750 that is removed can extends along all or substantially the entire distal leg 727. In some embodiments, the depth of the portion 755 of the second layer 750 that is removed can be sufficient to expose the first layer 760. Alternatively, the depth of the material removed can be less than the depth of the second layer so as not to expose the first layer. Additionally, the removed portion 755 can create a tapered distal leg 727. As embodied herein, for purposes of illustration and not limitation, the outer layer material is removed about the second segment 740 of the distal leg, sufficient to expose the first layer 760 along the length of the second segment 740 of the distal leg. The length of the second segment 740 of the distal leg can be of any suitable diameter, for example, approximately 0.5 mm for a dilation catheter.

As noted in FIG. 9, a distal section 712 of the inner tubular member 710 is positioned (640) in the balloon 720 with at least a length of the second segment 740 of the distal leg 727 extending beyond the distal end 715 of the inner tubular member 710. The first segment 730 of the distal leg 727 can be disposed proximate the distal section 712 of the inner tubular member 710. The second segment 740 of the distal leg 727 can extend distally beyond the distal end 715 of the inner tubular member 710 in its entirety. For example, in some embodiments, the distal end 712 of the inner tubular member 710 can be disposed beyond the first segment 730 but not beyond the second segment 740. In other embodiments, the distal section 712 can be disposed such that the distal end 715 is proximate a portion of the first segment 730. As embodied herein, the inner member 710 is positioned about the length 730 and the length 730 is about 0.5 to about 4 mm. The inner tubular member 710 is bonded (650) to the first distal leg segment 730 of the balloon 720. For example, in one embodiment, electromagnetic energy, such as thermal energy, can be applied to the distal leg 727 of the balloon 720 to bond at least a portion of the first segment 730 to the distal section 712 of the inner tubular member 710. Applying heat to the distal leg 727 of the balloon can cause the polymeric material of the balloon 720 to soften, or melt and flow. The first segment 730, in its softened or molten state, can form a bond with the distal section 712 of the inner tubular member 710.

As with methods discussed with reference to FIG. 3, through FIG. 5 above, similar techniques likewise can be applied to the multilayer balloon. For example, a mandrel can be positioned (641) in the lumen 717 of the inner tubular member 710. The mandrel can, for example, be tapered such that the portion of the mandrel extending distally beyond the distal end 715 of the inner tubular member 710 decreases in diameter. The mandrel can be positioned such that it extends beyond the second segment 740 of the distal leg 727 of the balloon 720. The mandrel can be composed of a suitable material, such as metal, ceramic, or the like.

Furthermore, a heat shrink tubing can be positioned around the outside of at least the first and second segments 730 and 740 of the balloon 720 as disclosed above with reference to FIG. 5 and with reference to FIG. 7 (641 through 643). The heat shrink tubing, when heated, can shrink and exert an inward radial force on the distal leg. Because the applied heat causes the second segment 740 to become molten or softened, the diameter of the second segment 740 can reduce and the second segment 740 can be forced, for example, to conform to the mandrel. As embodied herein, solid state laser heating as already described is performed to heat the heat shrink tubing.

Additionally, it is noted that removing at least a portion of the second layer can be performed after the inner tubular member and the distal leg segment are bonded together. In this manner, additional aspects of the method described above with regard to FIG. 3 through FIG. 5 also can be employed. That is, the multilayer balloon 720 can be formed such that the first segment 730 has a first diameter and a first wall thickness and the second segment 740 has a second diameter and a second wall thickness as shown in FIG. 5 and with reference to FIG. 4 and FIG. 7 (621 through 624). The second diameter can be larger than the first diameter. At least a portion of the second layer can be removed from the second segment 740. The multilayer balloon will be formed and bonded in a manner as previously described. Once bonded, at least a portion of the second layer can then be removed as described.

To the extent not previously discussed herein, the various catheter components may be formed and joined by conventional materials and methods. For example, inner tubular member can be formed by conventional techniques, such as by extruding and sometimes necking constructs found useful in intravascular catheters as disclosed in U.S. Pat. Nos. 6,277,093 and 6,217,547, each of which is incorporated by reference in its entirety. Additionally, although not illustrated, coiled or braided reinforcements may be included in the shaft at various locations, as is conventionally known as disclosed in U.S. Pat. No. 7,001,420 which is incorporated by reference in its entirety.

While the present invention has been described herein in terms of certain preferred embodiments, those skilled in the art will recognize that modifications and improvements may be made without departing from the scope of the invention. For example, although the catheter illustrated in FIG. 1 is an over-the-wire balloon catheter, the catheter of the invention may be a variety of suitable balloon catheters, including rapid exchange type balloon catheters having a guidewire proximal port located distal to the proximal end of the shaft, a guidewire distal port in the distal end of the shaft, and a relatively short guidewire lumen extending therebetween. While individual features of one embodiment of the invention may be discussed or shown in the drawings of the one embodiment and not in other embodiments, it should be apparent that individual features of one embodiment may be combined with one or more features of another embodiment or features from a plurality of embodiments.

The invention claimed is:

1. A method of fabricating a balloon catheter, comprising:
providing an inner tubular member having a distal section, a distal end, and a lumen extending therein;
forming a balloon having a working length, a distal neck, and a distal leg, the distal leg having a first segment with a first diameter and first wall thickness and a second segment with a second diameter and second wall thickness, the second diameter being larger than the first diameter and the second wall thickness being thinner than the first wall thickness;
positioning the distal end of the inner tubular member in the balloon, with the first segment of the distal leg disposed proximate the distal section of the inner tubular member and the second segment of the distal leg extending distally beyond the distal end of the inner tubular member;

heating the distal leg of the balloon to bond at least a portion of the first segment to the distal section of the inner tubular member and to reduce the second diameter of the second segment of the distal leg.

2. The method of claim 1, wherein the inner tubular member comprises a material selected from the group consisting of nylon, polyurethane, polyethylene, co-polyamide polyester, and co-polyester.

3. The method of claim 1, wherein the balloon comprises a material selected from the group consisting of nylon, polyurethane, polyethylene, co-polyamide, polyester, and co-polyester.

4. The method of claim 1, wherein forming a balloon comprises:

melt-extruding a thermoplastic polymeric material to form a tube having a distal leg, the distal leg having a first segment and a second segment, and cooling the extruded tube to a temperature less than an elevated temperature of the melt-extrusion;

placing the extruded tube within a capture member, the capture member having a first portion with a first diameter and a second portion with a second diameter; and biaxially orienting the polymeric material of the extruded tube by radially expanding the extruded tube with pressurized media in the tube lumen and axially stretching the extruded tube with a load applied on at least one end of the tube, thereby forming a balloon having a distal leg, the distal leg having a first segment with a first diameter and first wall thickness and a second segment with a second diameter and second wall thickness, the second diameter being larger than the first diameter and the second wall thickness being thinner than the first wall thickness.

5. The method of claim 1, further comprising positioning a mandrel in the lumen of the inner tubular member, the mandrel extending beyond the second segment of the distal leg of the balloon.

6. The method of claim 1, further comprising positioning a heat shrink tubing around the outside of at least the first and second segments of the distal leg of the balloon.

7. The method of claim 1, wherein heating further comprises solid state laser heating, convection heating, or induction heating.

8. The method of claim 1, wherein the balloon is a multilayer balloon.

9. The method of claim 8, wherein the multilayer balloon further comprises:

a first layer made of a first polymer material having a first durometer; and at least a second layer made of a second polymer material having a second durometer, the second durometer being greater than the first durometer.

10. The method of claim 9, wherein the first layer comprises a material having a durometer between about 55D and about 63D.

11. The method of claim 10, wherein the material of the first layer is selected from the group consisting of polyurethane, polyethylene, co-polyamide, polyester, and co-polyester.

12. The method of claim 10, wherein the material of the first layer comprises polyether block amide.

13. The method of claim 9, wherein the second layer comprises a material having a durometer between about 70D and 72D.

14. The method of claim 13, wherein the material of the second layer is selected from the group consisting of polyamide, polyurethane, polyethylene, co-polyamide, polyester, and co-polyester.

15. The material in claim 14, wherein the material of the second layer comprises polyether block amide or polyamide.

16. The method of claim 9, wherein the second layer is an outer layer relative to the first layer, the method further comprising removing at least a portion of the second layer from the second segment of distal leg of the balloon.

17. The method of claim 16, wherein removing at least a portion of the second layer further includes removing at least a portion of the second layer from the first segment.

18. The method of claim 16, wherein the at least a portion of the second layer is removed with a rotary device.

19. The method of claim 16, wherein the at least a portion of the second layer is removed by milling or laser ablation.

20. The method of claim 16, further comprising monitoring the second layer to determine a removal depth; and terminating the removing at least a portion of the second layer when the removal depth reaches a predetermined threshold.

21. The method of claim 16, wherein removing the at least a portion is performed after bonding the inner tubular member to the first distal leg segment of the balloon.

22. The method of claim 1, further comprising:

positioning a mandrel in the lumen of the inner tubular member, the mandrel extending beyond the second segment of the distal leg of the balloon;

positioning a heat shrink tubing around at least a portion of the first and second segments of the distal leg of the balloon; and heating the heat shrink tubing and first and second segments of the distal leg of the balloon, to bond at least a portion of the first segment to the distal section of the inner tubular member.

23. The method of claim 1, wherein the inner tubular member comprises polyether block amide.

24. The method of claim 1, wherein the balloon comprises polyether block amide.

* * * * *